United States Patent [19]

Carson

[11] Patent Number: 5,028,594

[45] Date of Patent: Jul. 2, 1991

[54] USE OF PHOTODYNAMIC COMPOSITIONS FOR CYTOTOXIC EFFECTS

[75] Inventor: Dennis A. Carson, Del Mar, Calif.

[73] Assignee: Naxcor, Menlo Park, Calif.

[21] Appl. No.: 290,453

[22] Filed: Dec. 27, 1988

[51] Int. Cl.$^5$ .................. G01N 33/53; C07K 3/08; A61K 31/40
[52] U.S. Cl. .......................... 514/23; 424/9; 514/2; 514/61; 514/825; 514/885; 514/908
[58] Field of Search ............... 514/23, 825, 885, 908, 514/2, 61; 424/9

[56] References Cited

U.S. PATENT DOCUMENTS

| | | | |
|---|---|---|---|
| 4,486,538 | 12/1984 | Bogoch | 514/908 |
| 4,672,028 | 6/1987 | Olson | 435/7 |
| 4,677,056 | 6/1987 | Dupont et al. | 435/7 |
| 4,683,295 | 7/1987 | Carson | 530/391 |
| 4,693,885 | 9/1987 | Bommer et al. | 530/331 |

Primary Examiner—Ronald W. Griffin
Attorney, Agent, or Firm—Richard L. Neeley

[57] ABSTRACT

Hematopoietic cells are selectively eliminated by cytotoxic agents which rely upon light activation. The cytotoxic agents are joined to ligands, particularly sugars, specific for myeloid monocyte and lymphocytic lineages. Further specificity can be achieved by limiting the light target. The method and compositions find particular use in organ transplants and arthritis.

27 Claims, No Drawings

USE OF PHOTODYNAMIC COMPOSITIONS FOR CYTOTOXIC EFFECTS

INTRODUCTION

1. Technical Field

The subject invention is related to the use of photoactive compounds for cytotoxic therapeutic effects.

2. Background

There is a general interest in being able to target specific cells or tissue for cytotoxicity. The cells or tissue may be diseased tissue or cells or in many cases healthy cells. The healthy cells may be involved in inhibiting a therapeutic treatment, such as in transplants or causing a disease state, such as in autoimmune diseases.

For example, organ transplantation can be lifesaving in diseases affecting the heart, kidneys, liver, and lung. It has also been shown that transplantation of dispersed pancreatic islet cells may completely cure diabetes, a common and debilitating disease. The major impediment to the more widespread use of transplantation is rejection of the donor tissue by the transplant recipient. In part, this problem has been overcome by the use of the immunosuppressive agent, cyclosporin-A. However, the renal toxicity, infection, and expense associated with cyclosporin-A treatment has impeded the widespread use of the drug.

Experiments on animal model systems suggest that the transplantation rejection phenomenon is triggered by cells in the donor organ that express class II histocompatibility antigens. Therefore, if these cells could be removed from the donor organ, or inactivated, transplantation could be successfully accomplished even across major histocompatibility barriers.

Experiments have suggested that besides T cells, monocytes and macrophages are the cells involved in triggering the rejection response. As a result, a number of laboratories are attempting to remove these cells from donor organs before transplantation. One method directs the A chain of the toxin ricin to the mannose receptors of the monocytes and macrophages. Using this technique, macrophages could be selectively removed from rat liver by treatment of the animals with the ricin-A chain. However, following cell death, the ricin-A chain is released into the plasma where it is conceivably toxic to other cell types. Another method uses monoclonal antibodies against macrophage cell surface proteins to remove the monocytes and macrophages from the donor organs. None of these procedures have found general usage, nor are they without undesirable side effects.

There are also autoimmune diseases, which are believed to be associated with hematopoietic cell attack of native tissue. Exemplary of these diseases are various forms of joint inflammations, particularly rheumatoid arthritis and psoriatic arthritis. Many of the procedures used for the treatment of arthritis have been directed to the reduction of inflammation. The use of steroids has many side effects and frequently cannot be employed because of the adverse effects on the patient. Since the cells which may be involved with the inflammatory response in the case of the autoimmune disease may be of a general function, substantially depleting the host of such types of cells may have adverse effects on the ability of the host to fight off infectious agents. Therefore, generalized reagents which kill off all macrophages and monocytes, cells which may be involved with the arthritic condition, may subject the host to infection.

There is therefore an interest in being able to selectively prevent the adverse effects resulting from activities of native tissue, where the activities may have both beneficial and debilitating effects on the host. Techniques which allow for elective responses will provide for protection for a transplanted organ, or from pathogens, while at the same time maintaining the immunological capability of the host.

Relevant Literature

Cell specific ligands which were found to be potent competitive inhibitors of the uptake of labeled D-mannose-bovine serum albumin conjugate by rat macrophages were disclosed by Ponpipom et al. *J. Med. Chem.* (1984) 24, 1388–1395. Synthetic glycopeptide substrates for receptor-mediated endocytosis by macrophages were described by Robins et al. *Proc. Natl. Acad. Sci. USA* 78:7294–7298. The IME-thioglycosides for attaching sugars to proteins were described by Lee et al. *Biochemistry* (1976) 18:3956–3963. The use of ricin-A chain to delete mannose receptor bearing cells from rat liver was described by Simmons et al. (1987) *Biochem Biophys. Research Comm.* (1987) 146:849–854. The presence of a cell surface receptor on macrophages that binds glycoproteins having terminal sugars with the mannose or glucose configuration was disclosed by Stahl et al. (1978) *Proc. Natl. Acad. Sci. USA* (1978) 75:1399–1403. Compositions and methods for the treatment of organs to be transplanted are provided. The method involves removing phagocytic cells from the tissue to be transplanted by contacting the tissue for transplantation with a cytotoxic agent comprising a central nucleus, at least one saccharide moiety, and a toxic component specific for the inhibition of DNA replication. The method can be used to treat any organ for transplantation including heart, kidneys, liver, lung, and pancreas. Tupikin et al., Rev Matologian (*Moskva*) (1983), p. 32-32 describes the use of tetracycline as a photoactivator in exposure to argon laser rays in zymosan arthritis in rats. See also Tupikin et al., *Voprosy Revmatizma* (1982), p. 39–41. Oseroff et al., *Proc. Natl. Acad. Sci.* USA (1986) 83:8744–8748 describes the selective cytolysis of human T-cell leukemia cells in vitro using mAb conjugated to the photosensitizer chlorin. Ohnishi, et al., *Jap. J. Ophthal.* (1987), 31:160–170 described the use of argon-laser photoradiation on monkey retina treated with hematoporphyrin.

Manyak, *J. Clin. Oncol.* (1988) 6:380–391 provides a review of photodynamic therapy. See also the references cited therein. Tshish and Bailey, *Anal. Biochem.* (1985) 144:132–141 describe a particular peptide photoaffinity agent which may be used for linking a polypeptide to a photoreceptor.

SUMMARY OF THE INVENTION

Photodynamic therapy is provided directed to hematopoietic cells involved with cellular attack on endogenous cells, particularly those cells involved with organ transplant rejection and autoimmune diseases such as arthritis. The method employs reagents having a ligand for binding to the cell target and a photoactivatable agent, which results in selective cytotoxicity upon exposure to light of the appropriate wavelength. As appropriate, light is specifically directed to the site of interest avoiding cytotoxicity of host cells removed from the site of interest.

DETAILED DESCRIPTION OF THE INVENTION

In accordance with the subject invention, novel methods and compositions are provided for destruction of hematopoietic cells associated with disease such as graft-versus-host disease, and autoimmune diseases. The method involves contacting the cells either directly or indirectly with a cytotoxic agent specific for hematopoietic cell targets, particularly macrophages and monocytes, and irradiating with light where the target cells are selectively killed.

In the case of transplants, the organ to be transplanted, removed from the donor, is contacted under appropriate conditions with the cytotoxic agent, irradiated with the appropriate wavelength, and may then be washed free of cells with the assurance that macrophages or monocytes will have been substantially depleted and, desirably, totally eliminated as viable cells.

In the case of autoimmune diseases where a specific site may be illuminated as in arthritis, the cytotoxic agent is generally administered to the host, and after sufficient time for dissemination of the agent throughout the host, the sites of the inflammation may be illuminated through the skin by employing an appropriate light source.

For the most part, the compounds or cytotoxic agents will employ a toxic component, normally a photoactivatable agent, the ligand which directs the toxic component to the hematopoietic target cell and a linking moiety. The ligand will normally be a saccharide moiety which shows specificity for binding to surface receptors of cytotoxic cells, particularly phagocytic cells, such as macrophages and monocytes.

Hematopoietic cells include phagocytic cells, helper T-cells and the like. Phagocytic cells are any cells which ingest microorganisms or other cells and foreign particles. In most cases, the ingested material is digested within the phagocyte. For purposes of the present invention, phagocytic cells include monocytes, macrophages, and other cells that are bound by the saccharide moiety and express class II histocompatibility antigens and trigger the transplantation rejection phenomenon. Monocytes include mononuclear phagocytic leucocytes which are formed in the bone marrow and are transported to the tissues, as of the lung and liver, where they develop into macrophages.

Cytotoxic T-cells include those cells which are, for the most part, CD8-positive and are involved with Class I MHC antigen and may include lymphokine-activated killer cells, natural killer cells, antibody-dependent cytotoxic cells or the like.

The instant method is effective in removing undesired hematocytes from cell tissue by directing an agent which is toxic to cells of the myeloid or T-cell lymphoid lineage but has no effect on other cell types. This is accomplished by directing the toxic agent to receptors which are specific to such cells. For example, mannose receptors are specific to phagocytic cells and are not detectable on any other cell type. Therefore, it is feasible to deplete mannose receptor bearing cells by directing a toxin to the mannose receptor containing cells.

The cell surface receptors of the phagocytes follow a recycling pathway. That is, the receptor binds a ligand dissociates and takes it from the cell surface where it is bound to an intracellular, prelysosomal acidic compartment, where the ligand dissociates from the receptor. The unoccupied receptor is returned to the cell surface for binding of more ligand. Thus, any cell which employs this receptor mediated pinocytosis for the selective efficient uptake of macromolecules can be selectively killed by the instant method. The cell surface receptors include those which bind and internalize injected glycoproteins. For binding to monocyte-macrophage cells, the preferred glycoproteins are those having terminal sugars with mannose or glucose configuration, preferably with terminal mannose molecules.

For cytotoxic T-cells, ligands other than sugars may be employed, which are specific for the cytotoxic T-cells. For example, various peptides may be employed which would bind to the CD8 protein or other receptors specific for the cytotoxic T-cells. These receptors include T-cell receptors and alpha-beta heterodimers. Alternatively monoclonal antibodies specific for cell types can be employed.

The cytotoxic agents which are employed will comprise the specific cell-directing ligand, the linking moiety, and the toxic component normally a photoactivatable agent. For the most part, the linking moiety will be either a bond or a small group or molecule of about 1 to 60 atoms other than hydrogen, more usually of about 1 to 20 atoms other than hydrogen. Conveniently, the linking group may be comprised of one or more amino acids, particularly those amino acids which have an additional functionality other than the carboxy or amino group of glycine. These amino acids include the basic amino acids, lysine and arginine, aspartic and glutamic acid, serine and threonine, cystine and histidine. In some instances it may be desirable to combine one or more amino acids to provide oligopeptides of about 2 to 10 amino acids. Of particular interest are oligolysines of from 2 to 4 units. When amino acids are used, they may be the natural L-enantiomer or the unnatural D-enantiomer or a racemic mixture. The linking groups may include functionalities, such as amides, esters, ethers, amines, thioethers, or the like. The various methods for linking the ligand and cytotoxic agent to the linking moiety may be varied widely and will follow conventional techniques. Thus, sugars, esters, ethers, and the like may be employed, particularly with substitution at the 1, 4, or 6 positions, or the like. For preparation of sugar derivatives, see, for example, Lee, et al. *Biochemistry* (1976) 15:3956–3963.

As the ligand, of particular interest will be saccharide molecules. Attached to the linking moiety may be a saccharide monomer or a polysaccharide. It may be desirable to utilize more than one saccharide monomer, a polysaccharide, as more than one sugar may be involved in binding to the receptor. For the present invention, preferably from about 1 to about 6 saccharide monomers will be utilized, more preferably about 3 to about 4 saccharide monomers.

Suitable saccharide molecules are any which bind specifically to the cell surface receptor site of interest. Since the present invention is involved in the elimination of particular cells, it will be desirable to utilize saccharide molecules which selectively bind to the cells of interest. Thus, as cells of the monocyte-macrophage lineage express specific receptors for mannose, and mannose receptors are not detectable on any other cell type, it will be particularly desirable to use mannose as the saccharide molecule.

Where more than one saccharide monomer is used, the polysaccharide may contain backbone linkages of any possible variation. For example, the sugars may be linked by either alpha or beta linkages in 1-2, 1-3, 1-4, or 1-6 fashion. However, as binding may be affected by the polysaccharide backbone, it may be desirable to construct the cytotoxic agent with a particular polysaccharide linkage. With mannose binding, although other constructions may be utilized, alpha-1,6 linkage is preferred.

For the most part, homopolysaccharides, that is, polysaccharides containing only one type of monomeric unit, will be utilized. As indicated earlier, homopolysaccharides of mannose units are preferred for the removal of phagocytic cells. However, if desirable, heteropolysaccharides, that is, those saccharides which contain two or more different monomeric units, may find use.

As disclosed earlier, recognition of carbohydrates by cells of binding proteins may require multivalency or clustering of saccharide residues, the various numbers of saccharide residues may be incorporated into the polysaccharide for binding to the linking moiety. These saccharide residues are introduced onto polypeptide backbones and these ligands used to deliver cytotoxic and therapeutic agents to saccharide receptor bearing cells.

Derivative forms of the monosaccharides may find use, such as glycosides, N-glycosylamines, O-acyl derivatives, and O-methyl derivatives. Examples of derivative forms of saccharide molecules, useful for binding to macrophage receptors, can be found in Ponpipom et al. (1981), *J. Med. Chem.* 24, 1388–1395, which is incorporated herein by reference. Where desired, the thiol forms of the saccharide derivatives may be employed.

The saccharide or polysaccharide molecule can be covalently attached to the linking moiety. For example, if trilysine is used as the backbone or linking moiety, saccharide molecules are covalently linked to the epsilon amino group. Alternatively, the polysaccharide molecule can be attached to the linking moiety by any number of techniques which have been developed for attaching sugars to proteins. Any of the known methods can be used including the mixed anhydride method, described by Ashwell (1972), *Meth. Enzymology* 28: 219, and the acyl azide method described by Lemieux et al. (1975), *J. Am. Chem. Soc.* 97, 4076. Also the use of diazonium salts, cyanoborohydride coupling agents, and 2-imino-2-methoxyethyl 1-thioglycosides, IME-thioglycosides, as described by McBroom et al. (1972) *Methods Enzymol.* 28, 212; Gray (1974), *Arch. Biochem. Biophys.* 163, 426; Moczar et al. (1975), *FEBS Lett.* 50, 300; and Lee et al. (1976), *Biochemistry* 15, 3956, respectively, may be employed. The conversion of the saccharide moiety to an IME-thioglycoside may be preferred as these IME-thioglycosides react readily with simple amines, amino acids, and proteins frequently without loss of any of the activity of the protein molecule. For use with macrophage receptor sites, mannosylating reagents that bind selectively to free amines have been described by Lee et al. supra, whose disclosure is incorporated herein by reference.

Since, for the purpose of the subject invention, the primary concern will be selection between the target cells and the other cells in the vicinity of the target cells, the ligand need not be specific for the target cells as against all other cells. It will be sufficient for the subject invention that the ligand be specific for the target cells, so as to distinguish between the target cells and the cells subjected to the light irradiation. Therefore other ligands which may be used which are specific for T-cells may include interleukins such as IL-2, IL-4, IL-5, and IL-6.

The toxic component will for the most part comprise photoactivatable agents which have found exemplification in the literature. These photoactivatable agents include coumarin, coumarin derivatives such as the psoralens, phthalocyanines, methylene blue, eosin, tetracycline, chlorophylls, various porphyrins, and the like. In many instances these compounds will have functionalities for linking to the sugars or to the linking moiety to provide for a stable linkage. The same types of linkages may be employed between the cytotoxic agent and the linking moiety as was described for linking the ligand to the linking moiety.

In some instances, particularly for the removal of the myeloid cells from transplantation organs, cytotoxic agents other than the photoactivatable agents may be employed. Such agents are well-known and may include a variety of DNA inhibitors such as anthacycline, daunomycin and adriamycin, amino-acridine derivatives such as mAMSA, cis-platinum derivatives, or the like.

In the case of transplantation, by transplantation is intended the transfer of tissue or organs from the body for grafting into another area of the same body or into another individual. Tissues to transplant include tissues, organs, and in some cases cells. Those transplants subject to the present method are any organs or tissues for transplantation, including but not limited to heart, kidneys, liver, lungs, pancreatic islet cells, bone marrow, stem cells, etc. The instant method is particularly useful for those organs that are very rich in monocytes and macrophages such as the pancreas, liver, and lung.

After surgical removal of the tissue or organ for transplantation, the organ is flushed with a preservative liquid, the perfusion medium. At the same time the temperature of the tissue or organ is lowered and the organ is maintained in a cold state, usually less than about 25° C., preferably about 4° C., so that its metabolic needs are kept at a minimum. After the chilling procedure is completed, the cooled organ is maintained at the low temperature by ice or refrigeration. Just prior to transplantation, the organ is again flushed using the same procedure as in chilling but in reverse. The perfusion medium used to flush the organ or tissue is progressively raised to a temperature level close to normal body temperature. Upon completion, the organ is in condition for transplantation.

By perfusion medium is intended the fluid which is pumped through the organ as well as the solution in which the organ or tissue is immersed. The cytotoxic agent is added to the perfusion medium used to maintain organs prior to transplantation to eliminate monocyte-macrophage cells. Cells of the monocyte-macrophage lineage ingest the conjugate, via their mannose receptors, and release the toxic agent, after digestion of the peptide in the endocytic vesicle. Uningested material and dead cells are washed out by perfusion, prior to transplantation of the organ or tissue.

Thus, the cytotoxic agent is included in the perfusion medium which is used to flush and maintain the organ prior to transplantation for a time sufficient to eliminate phagocytic cells. The cytotoxic agent can be included in the perfusion medium at any stage of the flushing or washing of the organ to be transplanted. The agent can be added to the perfusion medium at a particular temperature during chilling or subsequent rewarming or, alternatively, it can be present during all phases of the washing and maintenance of the organ or tissue. In all cases, it will be desirable to wash the organ to be transplanted with liquid minus the cytotoxic agent prior to transplantation. As binding of the cytotoxic agent occurs more readily between about 25° to about 37° C., it will be preferable to include the cytotoxic agent in the preservative medium at this temperature.

The tissue to be transplanted is washed with the perfusion medium containing the agent for about ½ hour to about 4 hours, preferably about 1 hour. With photoactivatable agents, the organ may then be thoroughly irradiated with light of the appropriate wavelength. Various means for irradiation may be employed, depending upon the nature of the particular organ. The light wavelength will desirably be greater than about 300 nm and may have a wavelength as high as 900 nm. After thorough irradiation, which may require anywhere from about 1 min to about 1 hr, preferably not more than about 30 min, the organ may then be flushed with perfusion medium minus the cytoxic agent to wash out any uningested agent prior to transplantation. In some instances it may be desirable to use the photoactivatable agent in conjunction with a cytotoxic agent which does not require photoactivation. Alternatively, one or more perfusions may be employed using one or another of the reagents by themselves or in combination.

The concentration of the cytotoxic agent contained in the perfusion medium during washing may vary according to the time of treatment, the temperature or pH of the medium, or the organ being treated. Normally the agent is included in the perfusion medium at a concentration of about 100µM to 10mM preferably about 1mM to 10mM.

The cytotoxic agent can be utilized with practically any perfusion medium. Where the perfusion medium contains no calcium ions, it may be useful to add calcium to the medium to facilitate saccharide binding. Further, as non-specific binding is increased greatly in the absence of serum, it may be necessary to add HSA, BSA or other acceptable protein to the liquid. For the most part, the pH of the liquid will be suitable for binding of the cytotoxic agent. A pH from about 6.6 to about 7.4 will usually be employed for greater binding of the cytotoxic agent to the cell surface receptor.

This method for treating organs to be transplanted can be used with any flushing procedure currently used. That includes those procedures which involve continuous gravity flow through the tissue, where the chilled liquid is dispersed from a solution bottle held at a height sufficient to produce a continuous gravity flow, or those procedures which involve mechanical washers, where the liquid is provided in pulsatory flow in a manner simulating the action of the circulatory system. After the donor organ or tissue has been treated with the cytotoxic agent and subsequently washed, the organ may be transplanted without releasing cytotoxic materials into the donor. In this manner, the phagocytic cells are eliminated from the tissue or organ to be transplanted and rejection of the tissue by the transplant recipient is prevented.

For treatment of arthritis, the agent may be administered generally to the host through the vascular system, or be injected directly into the site to be treated. The determination of whether the drug should be generally or specifically administered will be a matter of the number of sites to be treated, the level of drug required and the like. Generally the concentration employed will provide for concentration at the site to be treated in the range of about 10µM to about 1mM, more usually about 10µM to about 100µM. Thus the concentration of the reagent will vary widely depending upon the manner of administration. Conveniently, the cytotoxic agent may be formulated in a suitable physiologically acceptable medium such as sterile water, phosphate-buffered saline, aqueous alcohol, or the like.

After administration of the photoactivatable cytotoxic agent, the sites to be treated will be subjected to light for a time to sufficiently activate the toxic component. Optical fibres may be directed to the skin site or allowed to penetrate a small distance into the skin. With larger areas to be illuminated, a plurality of optical fibres may be employed or, alternatively, various irradiation lasers may be employed. The intensity of the light will vary depending upon the level required, the distance the light must penetrate, and the like. The energy delivered will vary, generally being in the range of about $0.1 mJ/cm^2$ to about $5000 J/cm^2$. After illumination, depending upon the manner in which the cytotoxic agent is administered, the patient may be required to be protected from light after the treatment.

The subject compositions may find alternative uses, particularly in research where it may be desirable to deplete various cellular preparations of a particular group of cells. Thus, rather than mechanical selection such as fluorescence-activated cell sorting, the subject methodology allows for relatively rapid specific removal of the undesired cells. The subject compositions may also find use in other applications besides research, where it is desired to remove a particular group of cells and the cells can be subject to irradiation.

The use of the cytotoxic agent as described and the treatment of organs or tissues to be transplanted offer several advantages over current methods for the treatment of donor tissue. First, the agent is selectively toxic to cells of the monocyte-macrophage lineage, but will have little effect on other cell types. This is accomplished first by designing the cytotoxic agent to bind only to cell surface receptors of the monocyte-macrophage cells. Secondly, the cytotoxic component utilized is designed such that it interacts tightly with the DNA and/or needs the appropriate light wave length for activation. Further, after ingestion by the phagocytic cells, there is no release of toxic materials to other cells.

Besides effectively eliminating the phagocytic cells, the cytotoxic agents are stable and easy to prepare. Furthermore, for use with transplants the drug would be used in vitro rather than in vivo and, therefore, would be washed out prior to transplantation.

The following examples are offered by way of illustration and not by way of limitation.

EXPERIMENTAL

Treatment of Arthritis

First, chlorin monoethylenediamine monoamide (chlorin $e_6$-A) is prepared by sequential addition of triethylamine and ethylchloroformate to chlorin $e_6$ dissolved in anhydrous dimethylformamide, as described by Oseroff et al. Proc. Nat'l. Acad. Sci. (1986) 83:8744. A 10-fold molar excess or ethylenediamine is then added to the monoactivated chlorin, and the product is purified by reverse phase HPLC on a $C_{18}$ column eluted with 0-55% methanol gradient in 0.1 M sodium phosphate pH 6.8. CNM thioglycomannoside is purchased from E.Y. Laboratories, and is converted to the 2- amino-2-methoxyethyl-1-thiomannoside by incubation in sodium methoxide. After evaporation, the residue is mixed in 0.1 M borate buffer pH 9 with a synthetic di-peptide consisting of lysine-lysine. After overnight incubation, reactants are separated by passage through a column of Sephadex G25 to remove the free thioglycoside. In this way, a trimannosyldilysine peptide is generated in which the epsilon amino groups are coupled to mannose. The mannosylated peptide is then mixed with the chlorin $e_6$-monoethylenediamine monoamide in the presence of a water soluble carbodiimide to couple the chromophore to the free carboxyl group of the peptide. Conjugate is separated by reverse phase HPLC as described above. This chlorin-trimannosyl peptide the active moiety for elimination of macrophages and other cells having mannosyl receptors.

In a typical in vitro experiment, human peripheral blood is obtained, and the mononuclear cell fraction is isolated by ficoll-hypaque sedimentation. Cells are suspended in RPMI 1640 medium supplemented with 5% autologous serum. Subsequently, the medium is supplemented with the chlorin-trimannosyl lysyl peptide. Then the cells are washed three times and suspended in RPMI 1640 medium supplemented with 10% autologous serum. The cells that have been incubated with the conjugate for 30 min at 4° C. are irradiated with a light source filtered to deliver light between 630-670 nm. The dose rate is typically 0.6 mJ/cm$^2$. Controls include unirradiated cells and cells which have been exposed to light, but not the photosensitizer. After radiation, cells are washed, and both immediate and delayed photocytotoxicity is assayed using ethidium bromide staining and fluorescence microscopy. In some experiments, lymphocytes are distinguished from monocytes and macrophages using monoclonal antibodies to the CD5 Pan-T cell antigen, and to immunoglobulin. Monocytes and macrophages are visualized by the binding of anti-Mac1 (anti-CD11b) antibodies. Selectivity is demonstrated by the elimination of viable monocytes and macrophages and the preservation of viability in the lymphocyte population.

In an in vivo experiment, adjuvant arthritis is induced in Spague Dawley rats by injection of complete Freund's adjuvant intradermally in the back. After the onset of joint swelling, the animals are injected intraperitoneally with the chlorin-peptide conjugates at dosages ranging from 0.1-10 mg/kg. At 4, 24, and 48 hrs after the injection the animals are anesthetized, and the immobilized limbs are selectively exposed to 630-670 nm light to yield a total dosage of approximately 50 J/cm$^2$. Control animals receive either light exposure alone, or treatment with the chlorin conjugate alone. After returning the animals to their cages, joint swelling is monitored daily. Efficacy of the treatment is indicated by accelerated reduction of joint swelling and inflammation in animals that have received the phototoxic therapy.

Depletion of Immunogenic Monocytes and Macrophages From a Donor Organ Before Transplantation First, tri-mannosyl dilysine is coupled to daunomycin using a water-soluble carbodiimide as described earlier. Conjugate is purified by reverse phase HPLC This daunomycin-trimannosyl peptide is the active moiety for the elimination of macrophages and monocytes from donor organs. In a typical experiment, an explanated kidney or liver from a rat is perfused at 4° C. with cold Collins storage solution, or with the same solution supplemented with 10-100 $\mu$M of the daunomycin peptide conjugate for 1 hr. Then the organs are flushed vigorously with Collins solution and maintained in the same for up to 48 hrs prior to transplantation into nephrectomized rats. Following transplantation, the animals are followed for signs of graft rejection, as indicated by rising blood urea nitrogen and serum creatinine. Rats that have received kidneys treated with the daunomycin peptide conjugates have prolonged maintenance of renal function, compared to control rats.

The subject invention provides for a convenient and efficient way to selectively remove cells which can be adverse to the host. By employing the subject technique, graft-versus-host disease can be avoided in the case of transplants, while substantial amelioration of inflammatory activity in joints may be substantially diminished without harm to the other tissue present and without substantially depleting the host of its immune capability.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for the destruction of hematopoietic cells capable of attacking host cells in vivo, to prevent cellular attack of endogenous cells, said method comprising:
    contacting cells with a cytotoxic agent comprising a cell-directing ligand specific for binding to said hematopoietic cells, a linking moiety and a photoactivatable toxic component; and,
    irradiating said cells with light at the appropriate wavelength for a time sufficient to kill said hematopoietic cells.

2. A method, as recited in claim 1, wherein said cell-directing ligand comprises at least one saccharide monomer.

3. A method, as recited in claim 2, wherein said saccharide monomer is mannose.

4. A method, as recited in claim 3, wherein said linking moiety comprises at least one amino acid.

5. A method, as recited in claim 4, wherein said amino acid is lysine.

6. A method, as recited in claim 1, wherein said photoactivatable agent is selected from coumarin, psoralens, phthalocyanines, methylene blue, eosin, tetracycline, chlorophyll, and porphyrins.

7. A method, as recited in claim 1, wherein said cell-directing ligand comprises peptides specific for cytotoxic T-cells.

8. A method, as recited in claim 1, wherein said hematopoietic cell comprises phagocytes, said linking moiety comprises trilysine, said cell directing ligand comprises four mannose residues.

9. A method, as recited in claim 1, wherein said hematopoietic cells comprises helper T-cells, said linking moiety comprises a group of about 1 to 60 atoms, other than hydrogen, and said cell directing ligand comprises a peptide ligand specific for cytotoxic T-cells.

10. A method for the selective destruction of hematopoietic cells involved in autoimmune diseases, from a host, said method comprising:
contacting said host with a cytotoxic agent comprising a cell-directing ligand specific for binding to said hematopoietic cells, a linking moiety and a photoactivatable toxic component; and,
irradiating specific sites of inflammation of said host for a time sufficient to kill said hematopoietic cells at said site, wherein the destruction of host cells away from the site of irradiation is avoided.

11. A method, as recited in claim 10, wherein said cell-directing ligand comprises at least one saccharide monomer.

12. A method, as recited in claim 11, wherein said saccharide monomer is mannose.

13. A method, as recited in claim 10, wherein said cell-directing ligand comprises peptides specific for cytotoxic T-cells.

14. A method, as recited in claim 10, wherein said photoactivatable agent is selected from coumarin, psoralens, phthalocyanines, methylene blue, eosin, tetracycline, chlorophyll, and porphyrins.

15. A method, as recited in claim 10, wherein said contacting step further comprises administering said cytotoxic agent through the vascular system of a patient and said irradiating step further comprises directing optical fibers or irradiation lasers to a treatment site for the selective removal of said hematopoietic cells.

16. A method, as recited in claim 10, wherein said contacting step further comprises injecting said cytotoxic agent directly into a site to be treated and said irradiating step further comprises directing optical fibers or irradiation lasers to said site.

17. A method for removing phagocytic cells from tissue for transplanting comprising contacting said tissue with a cytotoxic agent comprising a specific cell directing ligand specific for binding to said phagocytic cells, a linking moiety and a toxic component specific for the inhibition of DNA replication wherein said cell-directing ligand comprises at least one saccharide monomer.

18. A method, as recited in claim 17, wherein said cell directing ligand comprises at least one mannose monomer, said linking moiety comprises at least one amino acid and said toxic component is selected from anthracyclines, amino-acridine derivatives and cis-platinum derivatives.

19. A method, as recited in claim 17, wherein said tissue is selected from the group consisting of heart, kidneys, liver, lung, and pancreas.

20. A method, as recited in claim 17, wherein said contacting step further comprises the addition of said cytotoxic agent to a perfusion medium used to maintain said tissue prior to transplantation.

21. A cytotoxic agent comprising a cell-directing ligand specific for binding to hematopoietic cells, a linking moiety and a toxic component which results in cytotoxicity upon exposure to light in the appropriate wavelength, wherein said cell-directing ligand comprises at least one saccharide monomer.

22. A cytotoxic agent, as recited in claim 21, wherein said saccharide monomer is mannose.

23. A cytotoxic agent, as recited in claim 22, wherein said linking moiety comprises at least one amino acid.

24. A cytotoxic agent, as recited in claim 23, wherein said amino acid is lysine.

25. A cytotoxic agent, as recited in claim 24, wherein said photoactivatable agent is selected from coumarin, coumarin derivatives, psoralens, phthalocyanines, methylene blue, eosin, tetracycline, chlorophyll, and porphorins.

26. A cytotoxic agent, as recited in claim 21, wherein said hematopoietic cell comprises phagocytes, said linking moiety comprises trilysine, said cell directing ligand comprises a tetramannose.

27. A cytotoxic agent, as recited in claim 21, wherein said hematopoietic cells comprises helper T-cells, said linking moiety comprises a small molecule of about 1 to 60 atoms, said cell directing ligand comprises a peptide specific for cytotoxic T-cells.

* * * * *